(12) United States Patent
Hirayama et al.

(10) Patent No.: US 6,299,838 B1
(45) Date of Patent: *Oct. 9, 2001

(54) TEST APPARATUS FOR ASSAYING A COMPONENT IN A LIQUID SAMPLE

(75) Inventors: Kouji Hirayama; Michio Naka, both of Kyoto (JP)

(73) Assignee: Kyoto Daiichi Kagaku Co., Ltd., Kyoto (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/726,170

(22) Filed: Oct. 4, 1996

(30) Foreign Application Priority Data

Oct. 6, 1995 (JP) .................................................. 7-296312

(51) Int. Cl.[7] ...................................................... G01N 33/48
(52) U.S. Cl. ................................ 422/58; 422/56; 422/61; 436/164; 436/169
(58) Field of Search ............................. 422/56, 58, 61; 436/164, 169, 177

(56) References Cited

U.S. PATENT DOCUMENTS

| 3,992,158 | * | 11/1976 | Przybylowicz et al. | 422/58 |
|---|---|---|---|---|
| 4,761,381 | * | 8/1988 | Blatt et al. | 422/57 |
| 5,366,902 | * | 11/1994 | Cox et al. | 422/58 |
| 5,435,970 | * | 7/1995 | Mamenta et al. | 422/56 |

FOREIGN PATENT DOCUMENTS

| 0207392A | 1/1987 | (EP) . |
|---|---|---|
| 0322669A | 7/1989 | (EP) . |
| 0487068A | 5/1992 | (EP) . |
| 0587222A | 3/1994 | (EP) . |
| WO9010869A | 9/1990 | (WO) . |

* cited by examiner

Primary Examiner—Lyle Alfandary-Alexander
(74) Attorney, Agent, or Firm—Sughrue, Mion, Zinn, Macpeak & Seas, PLLC

(57) ABSTRACT

A test apparatus for assaying a component in a liquid sample by measuring a reflected light, comprising a support having a through hole or a light permeable area, a reagent layer having a detecting area fixed on the support to cover said through hole or light permeable area, and a cover which covers at least the detecting area, wherein at least a portion of the cover covering the detecting area is of a color which substantially has no influence on the reflected light at a measured wavelength.

1 Claim, 2 Drawing Sheets

TEST APPARATUS FOR ASSAYING A COMPONENT IN A LIQUID SAMPLE

FIELD OF THE INVENTION

The present invention relates to a test apparatus which is used for assaying a specific component contained in a liquid sample, especially a blood sample such as whole blood and serum, and a body fluid such as urine and cerebrospinal fluid by a color reaction. More particularly, the present invention relates to a test apparatus using reflected light as a measuring means.

BACKGROUND OF THE INVENTION

In order to measure a specific component in a liquid sample quickly and simply, for example, glucose, cholesterol or the like in a blood sample, or glucose, hemoglobin or the like in a body fluid sample, a dry type test apparatus comprises a support having thereon a reagent layer containing at least a reagent capable of developing a color by a reaction with the specific component.

When the test apparatus is used, the reaction starts by the supply of a liquid sample to one side of the reagent layer.

A color density of the developed color on the reagent layer after the reaction with a specific component corresponds to the amount of the specific component in the liquid sample. Accordingly, the specific component in the liquid sample can be determined by measuring the color density. The color density of the developed color on the reagent layer is measured by applying an incident light to the reagent layer after the color reaction and detecting intensity of the resulting reflected light or transmitted light.

Test apparatuses using reflected light can be divided roughly into two types from the viewpoint of sample supply to the reagent layer; one is a test apparatus having a sample-supplying area and a detecting area (namely, an incident light side area) on the same side, and another is a test apparatus having a sample-supplying area and a detecting area on different sides.

The test apparatus having a sample-supplying area and a detecting area on the same side is useful in measuring samples having high transparency such as sera and urine, but not suitable for measuring having low transparency such as whole blood.

On the other hand, the test apparatus having a sample-supplying area and a detecting area on different sides is markedly advantageous, because it is fully possible to measure a sample having low transparency such as whole blood by forming a reflection layer or a separation layer on the reagent layer.

In the test apparatus having a sample-supplying area and a detecting area on different sides, however, not only the reagent layer but also the structure of the test apparatus itself become complex in comparison with the test apparatus having a sample-supplying area and a detecting area on the same side. Accordingly, new components are often required in addition to the reagent layer and support. Examples of the test apparatus having a sample-supplying side and a detecting side on different sides include those which are disclosed in JP-A-55-59326 and JP-A-4-188065 (the term "JP-A" as used herein means an "unexamined published Japanese patent application").

The reflection layer is provided in order to clarify a coloring degree of the reagent layer by reflecting the injected light, and white particles of titanium dioxide or the like are used as its material. The usually used reflection layer has a thickness of from 2 $\mu$m to 50 $\mu$m. Also, light reflection capacity is added to the reagent layer itself by kneading titanium dioxide with a reagent in the reagent layer.

However, the reflection layer has a disadvantage in that it cannot perform complete reflection of light so that the light partially passes through the layer. When the thickness of the light reflection layer is increased in order to prevent such an unnecessary passage of light, the permeability of the liquid sample becomes poor so that proper results cannot be obtained.

In the case of the test apparatus of JP-A-4-188065, the portion corresponding to the reagent layer, as shown in FIG. 2 in expanded view, comprises a porous membrane to be used as a sample-holding layer, a reagent layer prepared from a reagent, a buffer, a binder and the like, a light reflection layer prepared from titanium dioxide which also acts as a blood cell filtration layer, a space where the supplied liquid sample passes, and a cover which forms a space above the reagent layer.

When light is injected into the reagent layer from the porous membrane side, types of the resulting reflected light are divided roughly into (1) light reflected from the porous membrane surface, (2) light reflected from the inner portion of the porous membrane and the inner portion of the reagent layer, (3) light reflected from the light reflection layer and (4) light reflected from the cover. Although necessary information among them is only the reflected light of (2) and (3), other types of reflected light are also measured. That is, the reflected light obtained by the injection of light is a mixture of several types of reflected light, and these unnecessary types of reflected light are generally measured as an error.

Even in the case of the same type of liquid sample such as whole blood, hemolytic serum, chromaturia or the like, the liquid sample itself sometimes shows different colors. For example, the color of whole blood varies depending on the difference in its hematocrit value and the like, and the color of serum varies depending on the difference in its degree of hemolysis and the like. Depending on the difference in the color of these liquid samples, coloration of the reagent layer varies and the amount of light passing through the reagent layer also varies.

When the measurement is carried out using reflected light, the light reflected from the cover provided on the side which is not the incident direction of the reagent layer (the aforementioned type (4) reflected light) is also simultaneously detected by its passage through the reagent layer, so that difference in the coloration of the reagent layer in each measurement causes changes in the amount of light which passes through the reagent layer and also the amount of the reflected light of type (4) which passed through the same, thus inevitably exerting unnecessary influence upon the measured values.

SUMMARY OF THE INVENTION

Therefore, an object of the present invention is to resolve the above-described problems concerning irregular measured values due to errors caused by the variation of color of each liquid sample in a test apparatus in which a specific component in a liquid sample is determined by measuring a reflected light.

In order to resolve the above problems, the inventors of the present invention have conducted intensive studies and found that the influence of unnecessary reflected light can be avoided when an area which has substantially no influence on the reflected light at a measured wavelength is provided on one side of a reagent layer opposite to the side where the light is incident, because the reflection of light passed through a reflection layer in the reagent layer is lowered in that area.

Accordingly, this and other objects of the present invention have been attained by a test apparatus for assaying a component in a liquid sample by measuring a reflected light comprising a support having a through hole or a light permeable area, a reagent layer having a detecting area fixed on the support to cover the through hole or light permeable area, and a cover which covers at least the detecting area, wherein at least a portion of said cover covering the detecting area is of a color which substantially has no influence on said reflected light at a measured wavelength.

DETAILED DESCRIPTION OF THE INVENTION

Figure 1:
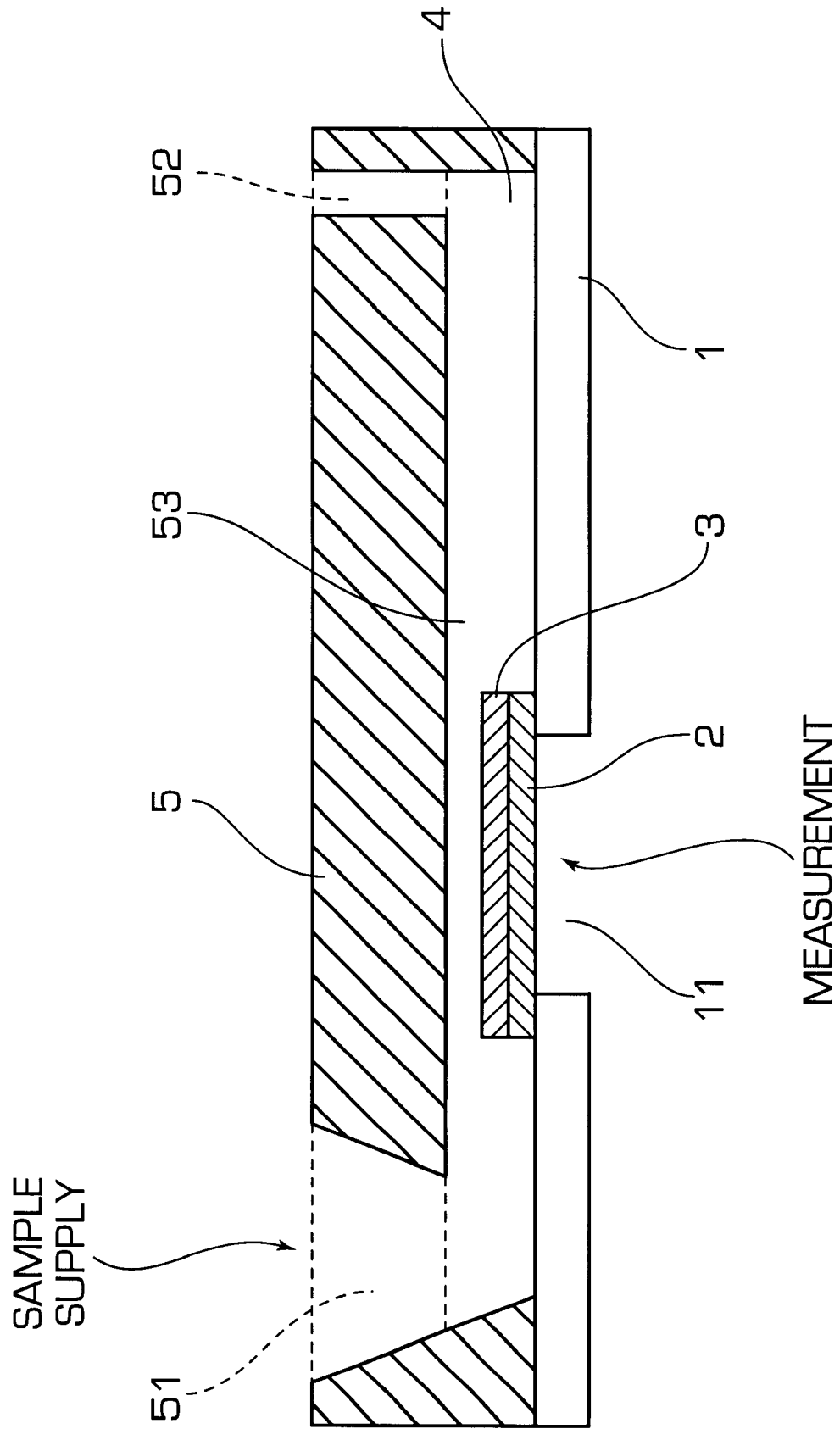
FIG. 1 is a sectional view of a test apparatus according to the present invention.
Figure 2:
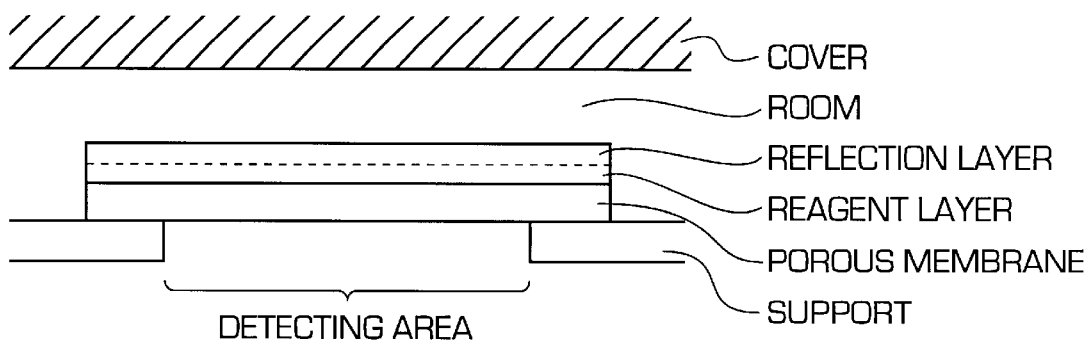
FIG. 2 is an expanded sectional view of the reagent layer and its surrounding area shown in FIG. 1.

The test apparatus for use in the present invention can have the following embodiments. One of them is a test apparatus having the same basic structure disclosed in JP-A-4-188065, in which its cover is fixed on a support in such a manner that a sample-holding room is formed between the reagent layer and the cover which has a sample-supplying hole and an air exhaust hole. This cover is of color which substantially has no influence on the reflected light at a measured wavelength (see sectional views of FIGS. 1 and 2, FIG. 2 is an expanded view of the reagent layer and its surrounding area of FIG. 1).

When this test apparatus is used, a liquid sample is added dropwise through the sample-supplying hole. The thus added liquid sample flows in the sample-holding room and reaches the reagent layer set at a halfway position of the sample-holding room. When the sample is whole blood, blood plasma alone is separated by the blood cell separating action in the reagent layer, and reacts with the reagent in a porous membrane which acts as a sample-holding layer.

The measurement is carried out by observing the porous membrane from the support side.

Figure 3:
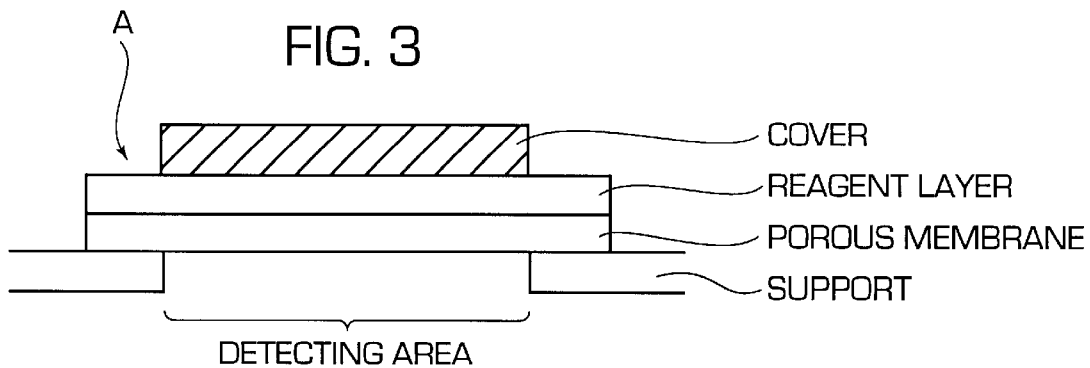
FIG. 3 is a sectional view of another example of test apparatus according to the present invention.

In another embodiment of the test apparatus, a cover is directly contacted with one side of a reagent layer opposite to the support (see FIG. 3). That is, the reagent layer is fixed on the support, and a portion of the reagent layer covered with the cover corresponds to the detecting area.

When this test apparatus is used, a liquid sample is spotted on position A of the reagent layer. Thereafter, the liquid sample flows into the reagent layer and is mixed therewith, and a reaction of blood plasma with the reagent occurs in the porous membrane which acts as a sample-holding layer. That is, the porous membrane of the test apparatus also acts as a matrix to transport the liquid sample.

According to the reagent layer of the present invention, it is preferable to coat or impregnate a base material with a coloring reagent for an enzyme reaction, a chemical reaction or the like. The base material has light permeability and is excellent in performing development and permeation of liquid. Examples thereof include matrices such as filter paper, cloth and glass filter, and gels such as gelatin.

Examples of the coloring reagent for use in the present invention include 4-aminoantipyrine, Trinder's reagents (e.g., DAOS, TOOS, MAOS), tetrazolium salts (e.g., NTB, TV, INT, MAOS), and p-nitrophenol.

The porous membrane may be provided between the reagent layer and the support. However, the porous membrane is merely a base which is effective in holding a necessary portion of liquid sample for carrying out the reaction and in coating the reagent on a layer. Accordingly, it is not particularly necessary for the construction of the present invention. Examples of the porous membrane for use in the present invention include polypropylene film (e.g., Celgard produced by Hoechest), polysulfone film (e.g., Filterite produced by Memtec), and polycarbonate film (e.g., Cyclopore produced by Whatman).

In the test apparatus of the present invention, it is preferable to form a light reflection layer on the reagent layer in order to facilitate observation of the coloring situation with the naked eye and to improve detection sensitivity by increasing the amount of light in the detecting area. With regard to properties and size of the light reflection layer, it is preferable to use such a thin and simple layer that it does not react with the reagent to be used in the reagent layer and with liquid samples, does not inhibit coloration of the reagent layer and can minimize its influence upon a permeation rate of liquid samples. Examples of the light reflective particles include titanium dioxide, magnesium oxide, and barium sulfate. They may be used alone, or polymer beads containing them may be used.

As described in the foregoing, unnecessary light passes through the light reflection layer when the light reflection layer is thinned in order to maintain a permeation rate of liquid samples. However, it is not necessary to take such unnecessary light into consideration in the present invention. In consequence, the reflection layer can be made into a simple structure (namely a thin layer) in order to increase the permeation rate of liquid samples, and a shortened measuring period can be expected because of the apparent increase in the liquid sample permeation rate. As an example of the reflection layer having a simple structure, the reagent layer and light reflection layer may be made into one body by kneading light reflective particles in the reagent layer, thereby adding light reflection function to the reagent layer itself.

The raw materials of the support and cover are not particularly limited, provided that they do not react with reagents and liquid samples in the reaction area and do not inhibit coloration of the reagent, or they are treated in advance for such purposes. Examples of the raw materials of the support include polyethylene terephthalate (referred to as "PET" hereinafter). Examples of the raw materials of the cover include plastics such as ABS resin, acrylics, polystyrene, and vinyl chloride.

With regard to the color tone of the cover, it is preferable to select a color which substantially has no influence on the reflected light at a measured wavelength. The color which substantially has no influence on the reflected light also means a color in which light reflection at a measured wavelength is lower or a color which fully absorbs a light of a measured wavelength. Specifically, the color has a reflectance of less than 30%, and preferably less than 10%. When the wavelength is 405 nm, a yellow cover is preferably used.

Black is preferred because of its advantages in that it can absorb light over a broad range of wavelengths and therefore can be applied to simultaneous measurement of a plurality of items.

Furthermore, a transparent cover is also preferred because of its advantages in that it does not reflect light over a broad range of wavelengths and therefore can be applied to simultaneous measurement of a plurality of items.

Examples of methods for preparing the cover are shown in the following.

(i) A method in which the cover is directly colored.
   (a) A pigment is kneaded with components (e.g., plastics) of a cover composition and then molded into a cover form.
   (b) A white cover is molded and then an entire portion or at least a part which corresponds to the reagent layer is colored by coating, seal-application or the like.
(ii) A method in which a transparent material is used for preparing a transparent cover.

The thickness of the layers constituting the test apparatus of the present invention is not particularly limited. For example, generally, the cover has a thickness of 100 to 500 $\mu$m, and the reagent layer has a thickness of 50 to 250 $\mu$m in a wet state and 3 to 15 $\mu$m in a dry state.

The present invention will now be illustrated in greater detail with reference to Examples, but it should be understood that the invention is not deemed to be limited thereto.

EXAMPLE 1

Test apparatus for use in the determination of blood glucose, in which its sample spotting side and detecting side are different from each other:

Composition of Reagent Solution

| | |
|---|---|
| Glucose oxidase | 10 ku |
| Peroxidase | 20 ku |
| 4-Aminoantipyrine | 150 mg |
| N-Ethyl-N-(2-hydroxy-3-sulfopropyl)-3,5-dimethylaniline | 200 mg |
| 0.15M Phosphate buffer (pH 7.0) | 2 ml |
| 4% Hydroxypropylcellulose | 3 g |
| 50 wt % Titanium dioxide solution | 1 g |

The test apparatus for use in Example 1 is similar to that shown in FIG. 1 and contains the structure of reagent layer and surrounding area thereof shown in FIG. 2. Dimensions such as width and the like are shown approximately for easy understanding by expanded sectional view.

Although the reagent layer and light reflection layer are divided with a dotted line in FIG. 2 for easy understanding, they are actually made into a composite as can be understood from the aforementioned formulation, so that the reagent layer also acts as a reflection layer.

A reagent solution of the aforementioned formulation was coated in a thickness of 100 $\mu$m on a light permeable porous film (Nuclepore) of 10 $\mu$m in thickness (2 in FIG. 1) and dried at 40° C. for 1 hour, thereby obtaining a reagent layer (3 in FIG. 1) which also served as a reflection layer. Thereafter, the resulting layer was cut to an area of 7 mm×7 mm.

The thus prepared apparatus of porous film, with its reagent layer up, was put on a support made of PET and coated with a thermoplastic resin (1 in FIG. 1) having a through hole of 4 mm in diameter (11 in FIG. 1) and then adhered to the support by thermo-compression bonding. A cover which was made of ABS resin and molded in a black color (reflectance: 5.3%, 5 in FIG. 1) was also put on the resulting support with its PET side downward and adhered by thermo-compression bonding, in order to cover the reagent layer and form a sample-holding room (4 in FIG. 1) between the cover and the support, thereby obtaining a test apparatus.

Since the cover (5 in FIG. 1) has a sample-supplying hole (51 in FIG. 1) and an air exhaust hole (52 in FIG. 1), a liquid sample added dropwise through the sample-supplying hole advances by capillary action and gravity flow action, getting over the reagent layer and wetting it. A portion of the sample reacted with the reagents enters into the porous film and is held therein.

A 20 $\mu$l portion of each of whole blood samples having the same glucose level but with varied hematocrit values as shown in Table 1 was added dropwise to the thus prepared test apparatus, and reflectance at 640 nm was measured 30 seconds thereafter from the porous film side through the through hole of PET using a color-difference meter. The thus obtained reflectance was converted into K/S value based on the formula of Kubelka-Munk. Results of the measurement are shown in Table 1.

EXAMPLE 2

A test apparatus was prepared in the same manner as in Example 1, except using a transparent cover (reflectance: 5%) instead of the aforementioned black-molded ABS resin. The obtained test apparatus was examined in the same manner as in Example 1.

Comparative Example 1

As a control, a test apparatus was prepared in the same manner as in Example 1, except using a cover molded in white-molded ABS resin (reflectance: 95%) instead of the aforementioned black-molded ABS resin.

In these examples, the shape of the test apparatus used herein is merely an example and therefore is not limited thereto.

TABLE 1

| Hematocrit (%) | Example 1 | | Example 2 | | Comparative Example | |
|---|---|---|---|---|---|---|
| | Reflectance (%) | K/S | Reflectance (%) | K/S | Reflectance (%) | K/S |
| 0 | 28.3 | 0.908 | 26.2 | 1.037 | 36.8 | 0.543 |
| 25 | 28.4 | 0.903 | 25.9 | 1.059 | 33.9 | 0.644 |
| 35 | 28.2 | 0.914 | 26.4 | 1.029 | 32.6 | 0.697 |
| 45 | 28.1 | 0.920 | 25.8 | 1.064 | 32.6 | 0.697 |
| 55 | 28.1 | 0.920 | 26.2 | 1.038 | 31.9 | 0.727 |
| 65 | 28.7 | 0.886 | 27.0 | 0.987 | 33.1 | 0.676 |

When measured using the test apparatuses of the present invention, fluctuations between maximum and minimum values of the reflectance and K/S value were found to be 0.6% or 1.2% and 0.034 or 0.77, respectively; on the other hand, such fluctuations were 4.9% and 0.184 when the control test apparatus was used.

Even when the values obtained with the hematocrit of 0% and 65%, which rarely to occur in reality, were excluded, fluctuations between maximum and minimum values of the reflectance and K/S value were found to be 0.3% or 0.6% and 0.017 or 0.035, respectively, when the test apparatus of the present invention was used; on the other hand, such fluctuations were 2.0% and 0.083 when the control test apparatus was used.

Thus, as has been described in the foregoing, since the test apparatus of the present invention is not influenced by unnecessary light reflected into the cover passing through the reflection layer in the reagent layer, the problem of fluctuation of the measured values due to difference in color of respective liquid samples can be resolved.

In addition, good results can be obtained even when the reflection layer is made into a simple structure for the purpose of increasing a permeation rate of liquid samples, and the thus increased permeation rate renders possible shortening of the measuring period.

While the invention has been described in detail and with reference to specific embodiments thereof, it will be apparent to one skilled in the art that various changes and modifications can be made therein without departing from the spirit and scope thereof.

What is claimed is:

1. A test apparatus for assaying a component in a liquid sample by measuring a reflected light, comprising:

a support having one of a through hole and a light permeable area, a reagent layer, having a detecting area, fixed on the support to cover one of the through hole and light permeable area, and a cover which covers at least the detecting area, wherein at least a portion of said cover covering the detecting area is of a color which substantially has no influence on the reflected light at a measured wavelength; and wherein said color is yellow.

* * * * *